United States Patent [19]
Chinn et al.

[11] Patent Number: 5,939,647
[45] Date of Patent: *Aug. 17, 1999

[54] SURFACE PARTICLE SAMPLING HEAD HAVING A ROTATABLE PROBE

[75] Inventors: Jeffrey D. Chinn, Foster City; Justin Lowe, Los Altos, both of Calif.

[73] Assignee: Applied Materials, Inc., Santa Clara, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/599,424

[22] Filed: Jan. 16, 1996

[51] Int. Cl.$^6$ ...................................................... G01N 1/08
[52] U.S. Cl. ...................................... 73/864.71; 73/864.33
[58] Field of Search ................................ 73/863.23, 864, 73/864.71, 864.72, 864.34, 864.33

[56] References Cited

U.S. PATENT DOCUMENTS

| | | | |
|---|---|---|---|
| 3,067,619 | 12/1962 | Fielding | 73/864.33 |
| 3,091,967 | 6/1963 | Hurdlow et al. | 73/864.71 |
| 3,362,141 | 1/1968 | Royster, Jr. et al. | 73/864.33 X |
| 3,430,496 | 3/1969 | Swanberg et al. | 73/864.71 |
| 3,843,198 | 10/1974 | Reynolds | 73/864.33 X |
| 4,615,513 | 10/1986 | Gibson et al. | 73/863.23 |
| 4,918,991 | 4/1990 | Bucher et al. | 73/864 |
| 5,243,865 | 9/1993 | Hsu et al. | 73/864.72 |
| 5,253,538 | 10/1993 | Swick et al. | 73/864.34 |
| 5,438,885 | 8/1995 | Zelazny | 73/864.71 |
| 5,500,369 | 3/1996 | Kiplinger | 73/864 X |

*Primary Examiner*—Thomas P. Noland
*Attorney, Agent, or Firm*—Thomason and Moser

[57] ABSTRACT

A surface particle sampling head having a rotatable probe The sampling head contains a handle, a probe and a joint connecting the handle to the probe such that the probe rotates relative to the handle. Preferably, the rotatable joint is a universal joint that enables the probe to gimbal relative to the handle. The probe further contains a manifold having a releasably attached face plate.

39 Claims, 4 Drawing Sheets

SURFACE PARTICLE SAMPLING HEAD HAVING A ROTATABLE PROBE

BACKGROUND OF THE DISCLOSURE

1. Field of the Invention

The invention relates to surface particle monitoring systems and, more particularly, to a surface particle sampling head for such systems.

2. Description of the Background Art

Surface particle monitoring equipment is used in semiconductor processing equipment to capture and analyze contaminant particles within a reaction chamber and, in general, within any cleanroom environment. Such analysis is particularly important following wet cleaning of a reaction chamber. The monitoring equipment is used to ensure that the cleaning procedures are sufficient to eliminate residual particulate contaminants, to determine sources of contaminants and to determine which cleaning procedures produce optimal cleaning results.

One example of surface particle monitoring equipment is the QIII manufactured by Dryden Manufacturing of Fremont, Calif. QIII is a registered trademark of Dryden Manufacturing. This equipment is the subject matter of U.S. Pat. 5,253,538, issued Oct. 19, 1993, the disclosure of which is incorporated herein by reference. The surface particle monitoring equipment contains a particle detector and a sampling head. The sampling head is also known in the art as a scanner. In use, the sampling head is positioned against a surface, e.g., an inner wall of a reaction chamber of a semiconductor processing system, to capture particulate contaminants on the surface. The particles are typically removed from the surface by air flow, e.g., a 1 cfm flow rate, that fluidizes the particles. Two hoses, or conduits, connect the sampling head to the particle detector such that air flow from one hose passes over the surface and fluidizes the particles that lie on the surface beneath the sampling head. From the sampling head, the particles are carried by the second hose to the particle detector.

The particle detector analyzes the captured particles to generate a particle concentration per inch (or centimeter) squared. Such concentration values are very useful in characterizing the effectiveness of chamber cleaning procedures.

The sampling heads used in the prior art are fabricated in a variety of sizes and shapes. For example, the probe, the portion of the sampling head that contacts the surface to be sampled, is available in various diameters, e.g., two inch or three inch diameter models. However, the probes form an integral portion of the sampling head and are not removable. As such, multiple sampling heads must be purchased to facilitate the use of various sized probes.

An additional disadvantage of the prior art sampling heads is that the surface of the probe (the face plate) is planar to match the typical surface shape encountered in semiconductor processing systems. Such planar face plates of the present probes limit the use of the sampling heads to effectively analyzing flat surfaces.

Other alternatives to the prior art sampling head structure include a handle that is either straight, i.e., the handle portion is in-line with the probe, or ninety degrees, i.e., the handle portion is orthogonal to the probe. In the prior art, the relative positions of the handle and probe are always fixed. Having a fixed position for the probe, makes it impossible for the sampling head to be used in certain applications where the sampling head will not fit into a portion of the chamber.

Therefore, a need exists in the art for a sampling head that is rotatable to allow for flexible positioning of the probe relative to the handle and to permit self alignment of the probe with the surface to be sampled. Also, it would be advantageous to have a detachable face plate that allows various shaped face plates to be easily interchanged.

SUMMARY OF THE INVENTION

The disadvantages heretofore associated with the prior art are overcome by the present invention of a surface particle sampling head having a rotatable probe. The inventive sampling head contains a handle, a probe and a rotatable joint, such as a universal joint, connecting the handle to the probe such that the probe rotates relative to the handle. The probe further contains a manifold having a releasably attached face plate.

More specifically, the manifold contains a source port that is coupled to a source of pressurized or compressed gas and a collection plenum that is coupled to a collection port that is, in turn, coupled to particle analysis equipment. The face plate contains a plurality of cam lock pin assemblies that interfit a plurality of cam locks located on the manifold. As such, the face plate is easily attached and detached from the manifold by rotating the face plate relative to the manifold. The face plate contains a center port that is coupled to the source port of the manifold. Additionally the face plate contains a circular collection channel that circumscribes the center port and is spaced apart therefrom. The collection channel is coupled, via a plurality of coupling ports, to the collection plenum of the manifold. O-ring gaskets provide a seal between the face plate and the manifold.

In operation, the face plate is positioned proximate a surface to be sampled. The compressed gas from the gas source is coupled, via hoses, to the source port in the manifold which, in turn, couples the gas to the center port of the face plate. The gas exits the center port, fluidizes any particles on the surface being sampled, and carries those fluidized particles to the collection channel. The gas flows radially from the center port to the collection channel. The particles are carried by the gas flow from the collection channel to the plurality of coupling ports into the collection plenum of the manifold. From the plenum, the gas flow carries the particles through the collection port to particle analysis equipment.

To ensure that the probe does not scratch or otherwise mar the surface being sampled, the face plate contains a ring channel that circumscribes the outer edge of the face plate. The ring channel supports a protective ring, fabricated of a flouropolymer such as a Teflon®, having a thickness that supports the surface of the face plate slightly above the surface being sampled. Teflon is a registered trademark of the E.I. du Pont de Nemours and Co. As an alternative to a ring, the surface of the probe can be impregnated with a flouropolymer or some other material to form a protective coating having a relatively low coefficient of friction.

The surface particle sampling head of the present invention is substantially more useful than the sampling heads of the prior art in that the present invention gimbals the probe such that surfaces that were previously deemed hard to reach with a conventional sampling head are now reachable because of the gimbaled probe. The gimbaled probe, in essence, self aligns to a parallel orientation relative to the surface to be sampled. Furthermore, the present invention allows for the use of varied face plate sizes and shapes that can be rapidly detached and attached from the manifold. Consequently, the invention allows surface particle sampling measurements to be made on surfaces and in locations that heretofore could not be measured with a prior art sampling head.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
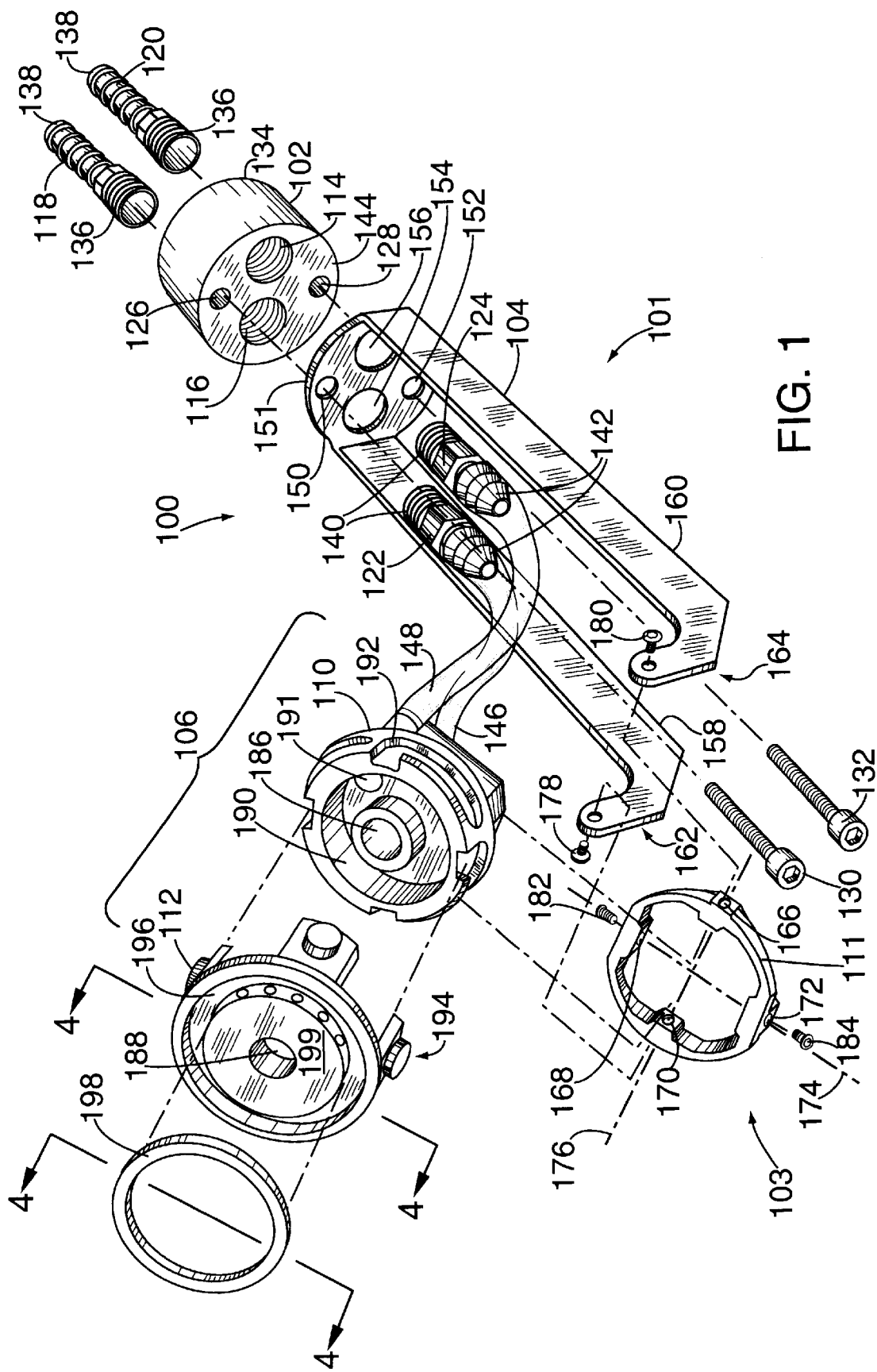
FIG. 1 depicts an exploded, perspective view of a gimbaled sampling head of the present invention.

FIG. 1 depicts an exploded perspective view of a sampling head 100 of the present invention. The sampling head contains a handle 101, a universal joint 103, and a probe 106. The handle contains a coupler 102 attached by screws 130 and 132 to a forked arm 104. The probe contains a manifold 110 removably attached to a face plate 112.

Specifically, the coupler 102 contains four threaded bores: two bores 114 and 116 (0.25 inch National Pipe Thread (NPT) holes) for attaching hose couplers 118, 120, 122, and 124 and two bores 126 and 128 for attaching forked arm mounting screws 130 and 132. The hose couplers 118 and 120 are threaded into bores 114 and 116 at end 134 of coupler 102. Each of these hose couplers have a threaded end 136 that interfits the bore threads and a ribbed (barbed) end 138 for attachment to a plastic hose (not shown). The plastic hose connects each hose coupler 118 and 120 of the sampling head to conventional particle monitoring equipment. Each of the hose couplers 122 and 124 also have a threaded end 140 that interfits the bore threads at end 144 of coupler 102 and a ribbed end 142 for attachment of plastic hoses 146 and 148. Typically, to avoid electrostatic retention of particles in the hoses, the plastic hoses are fabricated from an anti-static material.

Screws 130 and 132 each pass through bores 150 and 152 to attach the base end 151 of forked arm 104 to end 144 of coupler 102. The forked arm also contains bores 154 and 156 that allow the hose couplers 122 and 124 to pass through the forked arm to the coupler 102.

The forked arm 104 has two arms 158 and 160 that extend approximately four inches from the coupler 102. These arms, in essence, form a handle for the probe 106. The probe 106 is attached to the distal end 162 and 164 of each arm via the universal joint 103. As such, the probe can pivot along two orthogonal axes 176 and 174. Consequently, the probe may contact a surface at virtually any angle relative to the forked arm (handle).

Although the preferred embodiment of the invention contains a universal joint, in a broader sense, the joint may be rotatable in only one dimension, e.g., where the probe is fixedly attached to the handle along one axis and rotatably attached to the handle along the other axis. Even such limited rotation of the probe relative to the handle provides improved utilization of the probe over the prior art sampling heads.

The probe 106 contains the manifold 110 and the face plate 112. The probe is attached to the handle via a manifold mount 111. More specifically, the manifold mount 111 in conjunction with its attachment screws 178, 180, 182, and 184 forms the universal joint 103 that attaches the probe 106 to the handle 101.

The manifold mount 111 has a circular plan form with four bores 166, 168, 170, and 172 that define two, orthogonal axes of rotation 174 and 176. The manifold mount 111 is rotatably affixed to the distal end 162 and 164 of each arm 158 and 160 along a first axis 176. The mount is affixed to the arms by screws 178 and 180 that pass through the arms and into threaded bores 170 and 166 in the manifold mount. The manifold 110 is similarly attached to the manifold mount 111. However, the manifold is rotatably affixed along a second axis 174 via screws 182 and 184 through bores 168 and 172 in the manifold mount 111. This mounting structure, i.e., rotatable mounting of the manifold and the handle along orthogonal axes, gimbals the probe relative to the handle.

The manifold 110 has two hose couplers (shown and described with respect to FIG. 3) press fit into bores therein. Of course, the couplers could also be attached by threading the bore and the couplers. The first hose 146 is coupled to a source port 186 and the second hose 148 is coupled to the collection port 191. The source port feeds air to the center port 188 in the face plate to fluidize the contaminants on a surface proximate the face plate. The collection port is coupled to the collection plenum 190 that circumscribes the source port 186. The manifold is described in greater detail with respect to FIGS. 2 and 3 below.

The face plate 112 is detachable from the manifold such that face plates having various shapes and sizes can be easily interchanged to conform the sampling head to any sampling task. The face plate is attached to the manifold by four, eighty degree cam locks 192 located on the outer surface of the manifold. A cam lock pin assembly 194 interfits the cam and, when the face plate pin assemblies are inserted into the cams and rotated eighty degrees, the face plate seals to the manifold.

To facilitate particle collection, the face plate contains a center port 188 coupled to the source port 186 and a circumferential collection channel 196 that is coupled to the collection plenum 190 of the manifold 110. Optionally, a Teflon ring 198 is positioned about the circumference of the face plate 112. The ring has a vertical dimension that, when the face plate abuts a surface, separates the surface 199 of the face plate from the surface being sampled. Consequently, the ring ensures that the probe does not scratch or otherwise mar the surface being sampled. A detailed description of the face plate is provided with respect to FIG. 4.

Figure 2:
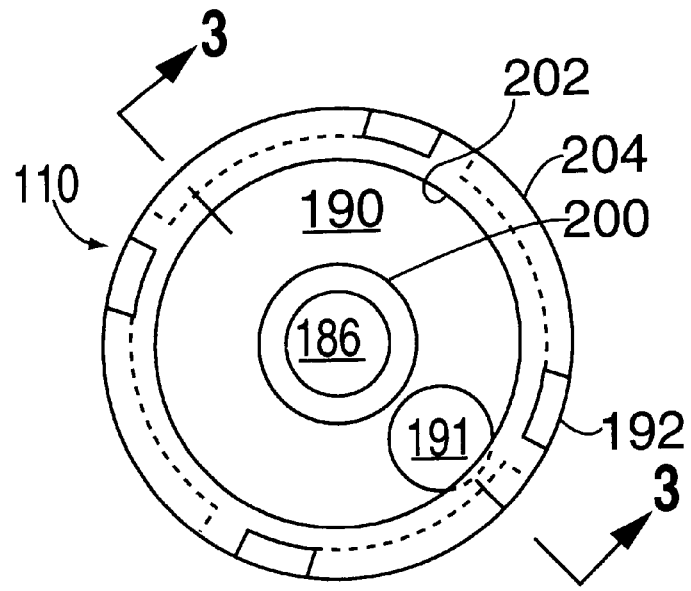
FIG. 2 is a top view of the manifold of the sampling head of FIG. 1.
Figure 3:
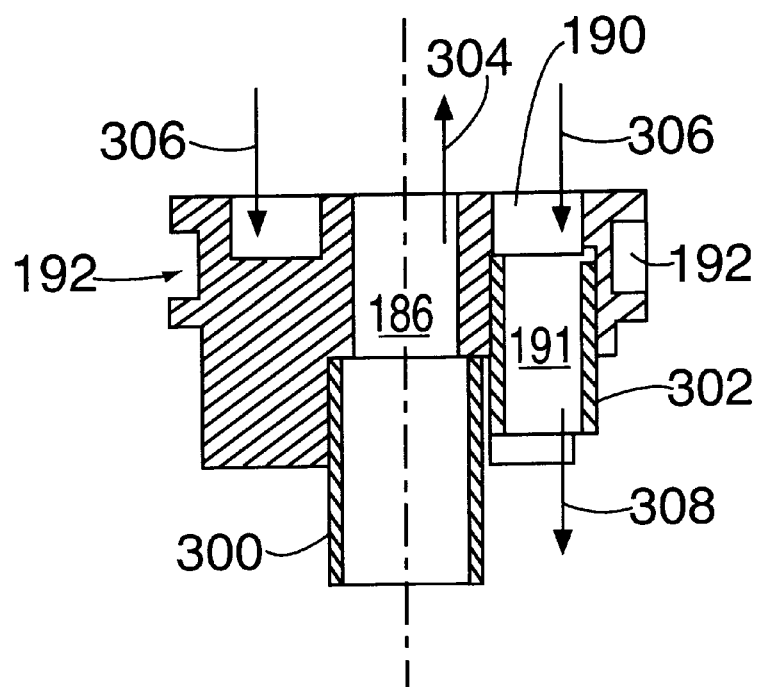
FIG. 3 depicts a cross-sectional view of the manifold of FIG. 2 taken along line 3—3.

FIG. 2 depicts a top view of the manifold 110 and FIG. 3 depicts a cross-sectional view of the manifold taken along line 3—3 of FIG. 2. The following description will refer to both FIGS. 2 and 3 simultaneously. The collection plenum 190 is defined by the outer wall 200 of the centrally located source port 186 and the inner wall 202 of the manifold 110. As such, the plenum has a torroidal shape with a collection port 191 coupled to the bottom of the plenum.

The outer wall 204 of the manifold contains four cam locks 192 located at ninety degree intervals about the circumference of the manifold. The cam locks are illustratively eighty degree locks, i.e., to lock the cam, the face plate must be rotated eighty degrees.

The manifold couples compressed air, or another gas, from the hose 146 through a hose coupler 300 to the source port 186. Similarly a hose coupler 302 is press fit into the manifold to couple hose 148 to collection port 191. A gas is pumped through source port 186, as indicated by the arrow 304. Gas returning from the face plate is coupled to the plenum 190 as indicated by the arrows 306. The plenum channels the gas to the collection port 191 where the gas exits the manifold as indicted by arrow 308. In this manner, particulate matter located on a surface that is proximate the face plate is fluidized by the gas from the source port. The fluidized particles are collected in the plenum and transported by the collection port through the various hoses and hose couplers of the handle, to the particle analyzing equipment. Alternatively, the compressed gas could flow in the opposite direction to that shown and the invention would still operate as an effective sampling head.

Figure 4:
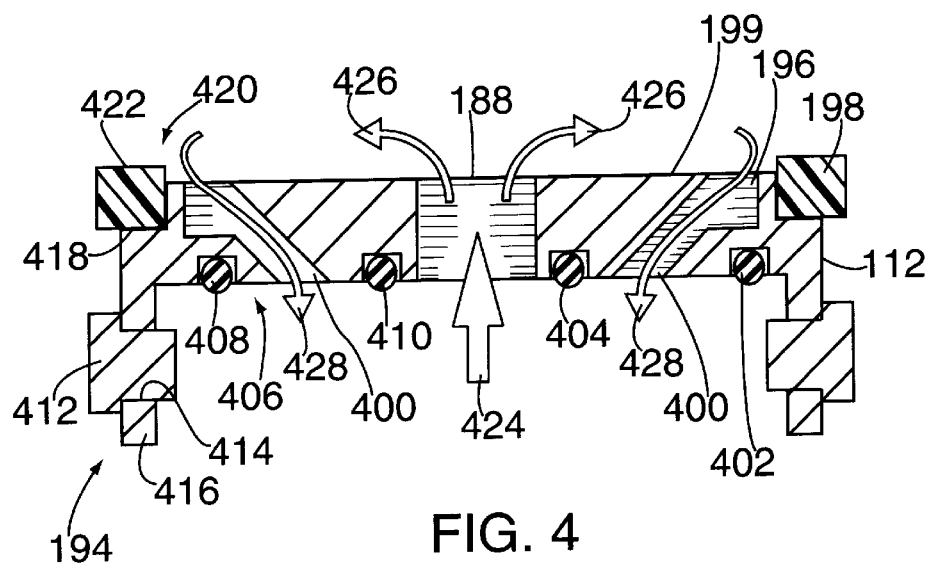
FIG. 4 depicts a cross-sectional view of a "small" face plate.

FIG. 4 depicts a cross-sectional view of the face plate 112. This face plate is referred to as a "small" face plate (diameter of approximately one inch) as opposed to the "large" face plate (diameter of approximately two inches). The large face plate is discussed with respect to FIGS. 5A, 5B and 6 below.

The small face plate of FIG. 4 is typically fabricated by milling a block of aluminum. The face plate 112 contains a center port 188 extending through the center of the face plate to couple with the source port of the manifold, a circumferential channel 196 coupled to the collection plenum of the manifold by a plurality of coupling ports 400 (e.g., eight coupling ports), circular gasket channels 402 and 404 located in the bottom surface 406 of the face plate, O-ring gaskets 408 and 410, and cam lock pin assemblies 194. Each cam lock pin assembly contains a pin 412 press fit in a bore 414 through a face plate finger member 416. The face plate contains four such cam lock pin assemblies that are each aligned with a cam lock of the manifold.

Additionally, the face plate 112 may optionally include a protective ring 198 located in a ring channel 418 circumscribing the outer edge 420 of the face plate. The vertical dimension of the ring, i.e., the ring's thickness, extends the ring surface 422 slightly above the upper surface 199 of the face plate. As such, when the face plate surface is positioned proximate a surface to be sampled, a pathway or channel is formed between the center port 188 and the collection channel 196. This pathway is defined by the surface being sampled and the upper surface of the face plate. To facilitate ease of motion across the surface being sampled, the ring is typically fabricated of a flouropolymer such as Teflon®. Teflon is a registered trademark of the E.I. du Pont de Nemours and Co. However, other materials may be used to fabricate the ring. One alternative to using a protective ring is to impregnate the entire surface of the face plate with a material such as a flouropolymer to form a protective coating.

In use, the pins 412 are inserted into the cam locks of the manifold and the face plate is turned clockwise eighty degrees. The cam locks force the face plate toward the manifold such that the gaskets 408 and 410 abut the surface of the manifold. The O-ring gaskets are typically fabricated from a resilient material such as rubber. Once the cam locks are locked, gasket 410 isolates the inflowing gas from the outflowing gas, and gasket 408 forms a barrier between the chamber environment and the return gas flow. In this manner, the source port of the manifold couples to the center port of the face plate and the coupling ports 400 couple the collection channel to the collection plenum of the manifold. The coupling ports are a plurality of inclined passageways connecting the collection channel to the plenum. A gas, typically air, is pumped through the source port and the center port 188. When the protective ring 198 of the face plate is positioned to abut a surface to be sampled, the surface to be sampled and the face plate surface 199 form a pathway or channel through which the gas flows from the center port 188 (arrow 424) to the collection channel 196. If the ring 198 is not used, the face plate surface 199 "floats" above the surface being sampled as air flows from the center port. Particulate matter on the surface being sampled is fluidized by the passing gas flow (arrow 426). The fluidized particles are carried by the gas through the collection channel 196, the coupling ports 400 and into the collection plenum of the manifold (arrows 428). As mentioned above, the sampling head also operates effectively when the gas flows in a direction opposite that shown.

The gimbaled probe enables the face plate to be rotated relative to the handle such that the face plate becomes flush with hard to reach surfaces. Furthermore, the use of cam locks enables the face plate to be interchanged with face plates of other shapes and sizes. These shapes and sizes vary depending upon the type of surface that is to be sampled.

Figure 6:
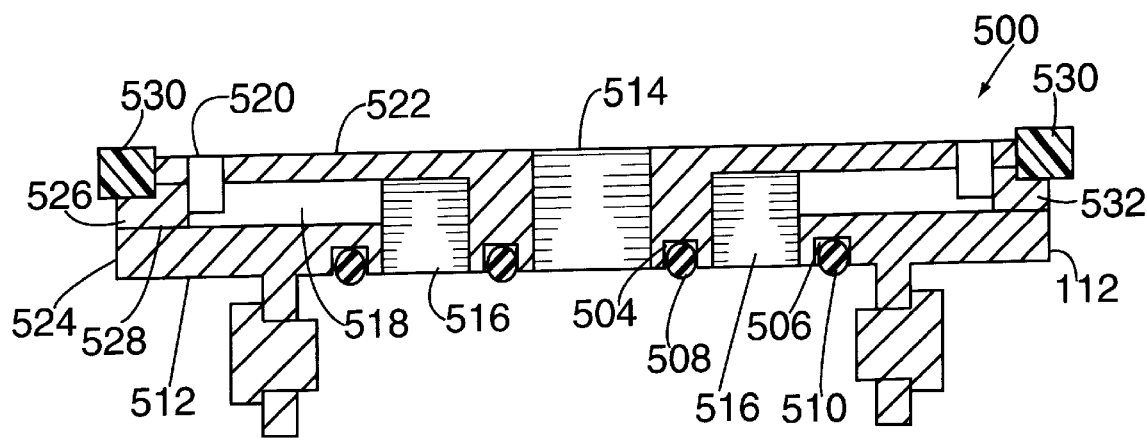
FIG. 6 depicts a cross-sectional view of the "large" face plate of FIGS. 5A and 5B taken along line 6—6.
Figure 5A:
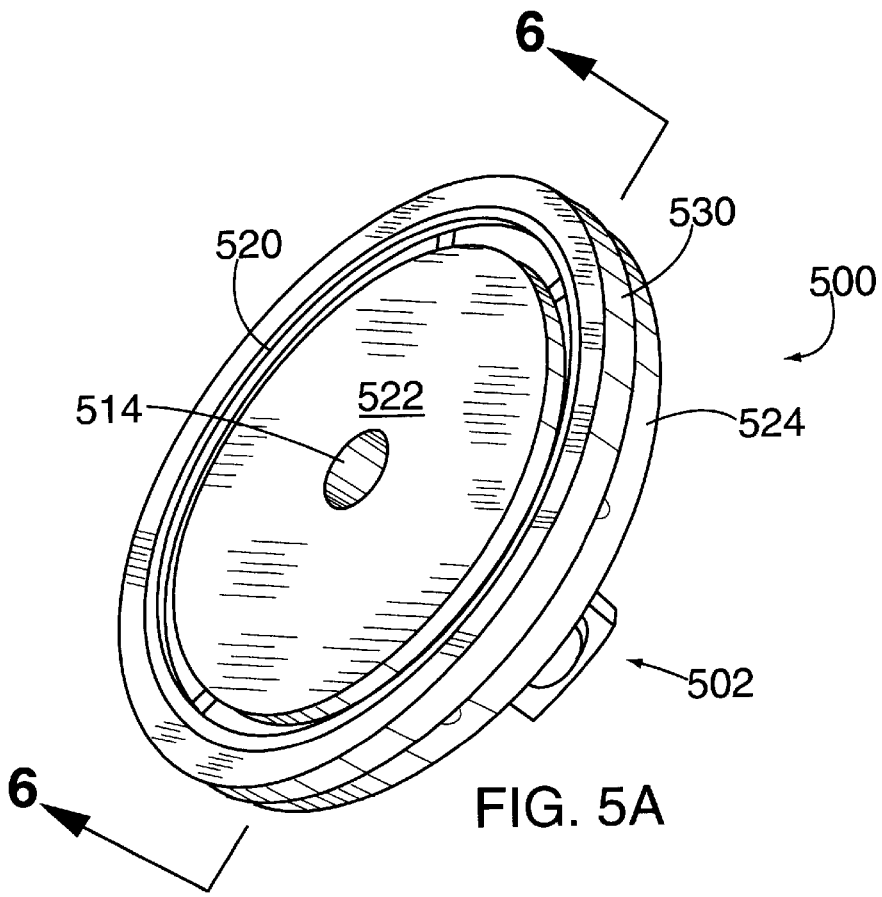
FIGS. 5A and 5B respectively depict a top and bottom perspective views of a "large" face plate.
Figure 5B:
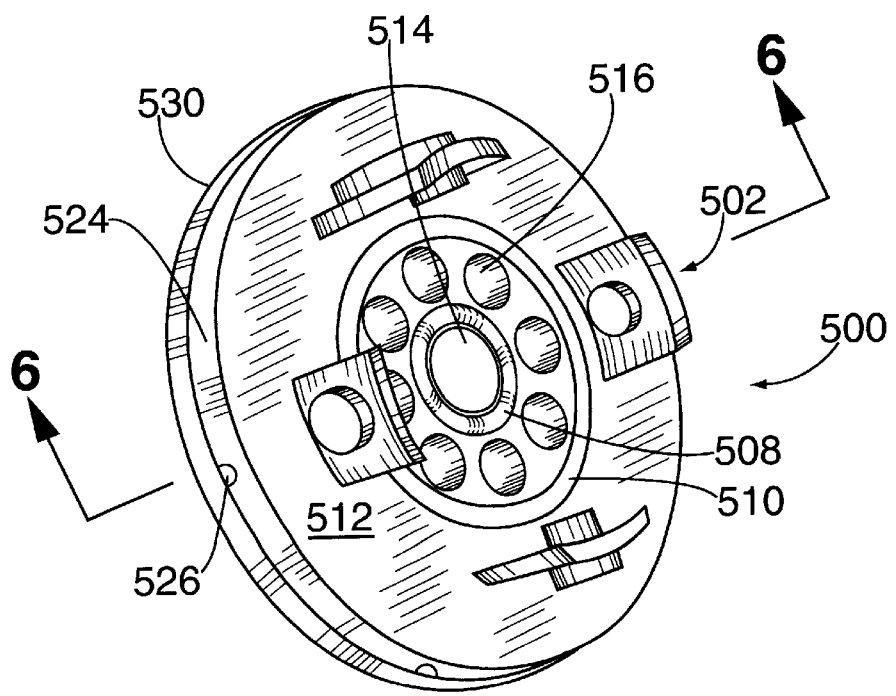

FIGS. 5A and 5B respectively depict a top perspective view and a bottom perspective view of a "large" face plate 500. Additionally, FIG. 6 depicts a cross-sectional view of the large face plate 500 taken along line 6—6 in FIGS. 5A and 5B. The large face plate has a diameter of approximately two inches. Structurally, the large face plate is substantially similar to the small face plate; however, there are a number of key differences that require separate disclosure.

Since all the face plates are interchangeable and releasably attach to the manifold cam locks, the cam lock pin assemblies 502, the locations of the gasket channels 504, 506 and gaskets 508, 510 on the lower surface 512 of the face plate 500, location of the center port 514 and the position of the openings 516 of the coupling ports 518 upon the lower surface 512 of the face plate are similar to the small face plate. As such, the gaskets 508, 510 align with the top surfaces of the manifold, the cam lock pin assemblies 502 align with the cam locks on the manifold, the center port 514 aligns with the source port and the openings 516 of the coupling ports 518 are aligned with the manifold plenum. Thus, the large face plate is interchangeable with the small face plate.

The large face plate has a substantially larger surface area along surface 522 between the center port 514 and the collection channel 520 than the small face plate. In fabricating the face plate, a plurality of openings 516 to the coupling ports 518 are drilled into the bottom surface 512 of the face plate. The circular collection channel 520 is then milled into the top surface 522 of the face plate. Because of the thickness of the face plate is small relative to the distance between the opening 516 and the channel 520, an inclined coupling port (as used in the small face plate) is difficult to fabricate. Therefore, the coupling ports 518 are each laterally drilled from the edge 524 of the face plate to connect the channel 520 with the openings 516. Then, a pin 526 or plug is press fit into end 528 of each coupling port 518 such that each coupling port connects an opening 516 to the channel 520.

In operation, the large face plate operates in exactly the same manner as the small face plate, i.e., a gas is pumped through the center port, particles are fluidized as the gas passes between the surface being sampled and the surface 522 of the face plate, the fluidized particles are collected in the collection channel, the collected particles are channels through one or more of the plurality of coupling ports to the collection plenum in the manifold. As with the small face plate, to avoid scratching or otherwise marring the surface being sampled, the large face plate is adapted to interfit with a ring 530 that is supported about the circumference of the face plate by a ring channel 532. As with the small face plate, the surface of the face plate can alternatively be coated with a protective material such as a flouropolymer.

Although the forgoing disclosure discussed two face plate embodiments: a small face plate and a large face plate, other face plate sizes and shapes may be useful in certain applications of the sampling head. For example, the surface of the face plate (522 in the large face plate and 199 in the small face plate) can be curved to match the curvature of a surface being sampled. Such a curved face plate is especially useful in the semiconductor processing art for sampling the interior wall surface of a cylindrical processing chamber. Using the principles of the invention, a face plate can be designed for the curvature of a particular chamber and rapidly interchanged with the flat face plates, as needed. Furthermore, although the disclosed face plates have circular plan forms, the face plates can be other shapes such as square, rectangular, oval, polygonal, and the like.

Although various embodiments which incorporate the teachings of the present invention have been shown and described in detail herein, those skilled in the art can readily devise many other varied embodiments that still incorporate these teachings.

What is claimed is:

1. A surface particle sampling head comprising:
   a handle;
   a probe for collecting particles from a surface; and
   rotatable joint, connected between said probe and said handle, for rotating said probe relative to said handle.

2. The surface particle sampling head of claim 1 wherein said handle further comprises a coupler for coupling a source of gas to the probe.

3. The surface particle sampling head of claim 1 wherein said rotatable joint is a universal joint.

4. The surface particle sampling head of claim 1 wherein said probe further comprises:
   a manifold; and
   a face plate releasably attached to said manifold.

5. The surface particle sampling head of claim 4 wherein said manifold further comprises:
   a source port coupled to a source of gas; and
   a collection plenum coupled to a collection port.

6. The surface particle sampling head of claim 4 wherein said face plate further comprises a plurality of cam lock pin assemblies which interfit a plurality of cam locks located on said manifold, whereby said face plate is releasably attached to said manifold.

7. The surface particle sampling head of claim 4 wherein said face plate further comprises:
   a center port for coupling to said source port of said manifold; and
   a collection channel, spaced apart from said center port, for coupling, via a plurality of coupling ports, to said collection plenum of said manifold.

8. The surface particle sampling head of claim 4 further comprising a gasket means, located between said manifold and said face plate, for sealing said manifold to said face plate.

9. The surface particle sampling head of claim 4 wherein said face plate further comprises circumferential ring channel supporting a protective ring.

10. The surface particle sampling head of claim 4 wherein said face plate further comprises a protective coating.

11. A surface particle sampling head comprising:
    a handle;
    probe means for collecting particles from a surface; and
    rotatable joining means, connected between said probe means and said handle, for rotating said probe means in at least one dimension relative to said handle.

12. The surface particle sampling head of claim 11 wherein said rotatable joining means comprises a gimbal means for gimballing said probe means relative to said handle.

13. The surface particle sampling head of claim 11 wherein said handle further comprises a coupler for coupling a source of gas to the probe means.

14. The surface particle sampling head of claim 11 wherein said rotatable joining means is a universal joint.

15. The surface particle sampling head of claim 11 wherein said probe means further comprises:
    a manifold; and
    a face plate releasably attached to said manifold.

16. The surface particle sampling head of claim 15 wherein said manifold further comprises:
    a source port coupled to a source of gas; and
    a collection plenum coupled to a collection port.

17. The surface particle sampling head of claim 16 wherein said face plate further comprises a plurality of cam lock pin assemblies which interfit a plurality of cam locks located on said manifold, whereby said face plate is releasably attached to said manifold.

18. The surface particle sampling head of claim 16 wherein said face plate further comprises:
    a center port for coupling to said source port of said manifold; and
    a collection channel, spaced apart from said center port, for coupling, via a plurality of coupling ports, to said collection plenum of said manifold.

19. The surface particle sampling head of claim 15 further comprising a gasket means, located between said manifold and said face plate, for sealing said manifold to said face plate.

20. The surface particle sampling head of claim 15 wherein said face plate further comprises circumferential ring channel supporting a protective ring.

21. The surface particle sampling head of claim 15 wherein said face plate further comprises a protective coating.

22. A surface particle sampling head comprising:
    a handle;
    a manifold that is releasably attached to a face plate for collecting particles from a surface; and
    a universal joint, connected between said manifold and said handle, for gimballing said manifold relative to said handle.

23. The surface particle sampling head of claim 22 wherein said manifold further comprises:
    a source port coupled to a source of gas; and
    a collection plenum coupled to a collection port.

24. The surface particle sampling head of claim 23 wherein said face plate further comprises:
    a center port for coupling to said source port of said manifold; and a collection channel, spaced apart from said center port, for coupling, via a plurality of coupling ports, to said collection plenum of said manifold.

25. The surface particle sampling head of claim 22 wherein said face plate further comprises a plurality of cam lock pin assemblies which interfit a plurality of cam locks located on said manifold, whereby said face plate is releasably attached to said manifold.

26. The surface particle sampling head of claim 22 further comprising a gasket means, located between said manifold and said face plate, for sealing said manifold to said face plate.

27. The surface particle sampling head of claim 22 wherein said face plate further comprises circumferential ring channel supporting a protective ring.

28. The surface particle sampling head of claim 22 wherein said face plate further comprises a protective coating.

29. A surface particle sampling head comprising:
a handle;
a probe, coupled to said handle, for collecting particles from a surface, said probe contains a manifold and a face plate releasably attached to said manifold.

30. The surface particle sampling head of claim 29 wherein said probe is coupled to said handle by a rotatable joint, connected between said probe and said handle, for rotating said probe relative to said handle.

31. The surface particle sampling head of claim 30 wherein said rotatable joint is a universal joint.

32. The surface particle sampling head of claim 29 wherein said handle further comprises a coupler for coupling a source of gas to the manifold.

33. The surface particle sampling head of claim 29 wherein said manifold further comprises:
a source port coupled to a source of gas; and
a collection plenum coupled to a collection port.

34. The surface particle sampling head of claim 33 wherein said face plate further comprises:
a center port for coupling to said source port of said manifold; and
a collection channel, spaced apart from said center port, for coupling, via a plurality of coupling ports, to said collection plenum of said manifold.

35. The surface particle sampling head of claim 29 wherein said face plate further comprises a plurality of cam lock pin assemblies which interfit a plurality of cam locks located on said manifold, whereby said face plate is releasably attached to said manifold.

36. The surface particle sampling head of claim 29 further comprising a gasket means, located between said manifold and said face plate, for sealing said manifold to said face plate.

37. The surface particle sampling head of claim 29 wherein said face plate further comprises circumferential ring channel supporting a protective ring.

38. The surface particle sampling head of claim 29 wherein said face plate further comprises a protective coating.

39. A surface particle sampling head comprising:
a handle;
a probe for collecting particles from a surface;
a coupler, attached to said handle, for coupling a source of gas to said probe;
universal joint, connected between said probe and said handle, for rotating said probe relative to said handle;
said probe containing a manifold and a face plate releasably attached to said manifold, where said manifold contains a source port coupled to a source of gas via said coupler and a collection plenum coupled to a collection port, where said face plate contains a plurality of cam lock pin assemblies which interfit a plurality of cam locks located on said manifold, whereby said face plate is releasably attached to said manifold, and said face plate contains a center port for coupling to said source port of said manifold and a collection channel, spaced apart from said center port, for coupling, via a plurality of coupling ports, to said collection plenum of said manifold; and
a gasket, located between said manifold and said face plate, for sealing said manifold to said face plate.

* * * * *